US011414380B2

(12) United States Patent
Boaz et al.

(10) Patent No.: US 11,414,380 B2
(45) Date of Patent: *Aug. 16, 2022

(54) AMPHOTERIC COMPOUNDS

(71) Applicant: Eastman Chemical Company, Kingsport, TN (US)

(72) Inventors: Neil Warren Boaz, Kingsport, TN (US); Stephanie Kay Clendennen, Kingsport, TN (US); Yuan Zhang, Gray, TN (US); Michael James Fevola, Belle Mead, NJ (US); Tobias Johannes Fütterer, Princeton, NJ (US)

(73) Assignee: Eastman Chemical Company, Kingsport, TN (US)

( * ) Notice: Subject to any disclaimer, the term of this patent is extended or adjusted under 35 U.S.C. 154(b) by 1008 days.

This patent is subject to a terminal disclaimer.

(21) Appl. No.: 14/856,656

(22) Filed: Sep. 17, 2015

(65) Prior Publication Data
US 2017/0081277 A1    Mar. 23, 2017

(51) Int. Cl.
| C07C 309/18 | (2006.01) |
| C07C 303/22 | (2006.01) |
| C11D 1/62 | (2006.01) |
| C07C 309/14 | (2006.01) |
| C07C 231/12 | (2006.01) |
| C07C 227/18 | (2006.01) |
| C07C 229/12 | (2006.01) |
| C07C 237/06 | (2006.01) |
| C09K 23/00 | (2022.01) |
| C07C 303/08 | (2006.01) |
| C09K 15/20 | (2006.01) |
| C09K 15/28 | (2006.01) |
| C12P 13/00 | (2006.01) |
| C12P 13/02 | (2006.01) |

(52) U.S. Cl.
CPC .......... C07C 309/18 (2013.01); C07C 227/18 (2013.01); C07C 229/12 (2013.01); C07C 231/12 (2013.01); C07C 237/06 (2013.01); C07C 303/08 (2013.01); C07C 303/22 (2013.01); C07C 309/14 (2013.01); C09K 15/20 (2013.01); C09K 15/28 (2013.01); C09K 23/00 (2022.01); C09K 23/018 (2022.01); C11D 1/62 (2013.01); C12P 13/001 (2013.01); C12P 13/02 (2013.01)

(58) Field of Classification Search
CPC ............. B01F 17/0042; B01F 17/0092; C07C 227/18; C07C 229/12; C07C 231/12; C07C 237/06; C07C 303/08; C07C 303/22; C07C 309/14; C07C 309/18; C09K 15/20; C09K 15/28; C12P 13/001; C12P 13/02
See application file for complete search history.

(56) References Cited

U.S. PATENT DOCUMENTS

| 2,781,349 | A | 2/1957 | Mannheimer |
| 3,001,997 | A | 9/1961 | Mannheimer et al. |
| 3,225,074 | A * | 12/1965 | Cowen ................... C07C 275/14 510/490 |
| 3,280,178 | A | 10/1966 | Barbour |
| 3,280,179 | A | 10/1966 | Ernst et al. |
| 3,915,882 | A | 10/1975 | Nirschl et al. |
| 4,259,191 | A | 3/1981 | Wagner |
| 4,687,602 | A | 8/1987 | Ballschuh et al. |
| 4,879,204 | A | 11/1989 | Ishigaki et al. |
| 5,696,070 | A | 12/1997 | Tachizawa et al. |
| 5,851,982 | A | 12/1998 | Sakata et al. |
| 5,972,877 | A | 10/1999 | Tsuda et al. |
| 6,365,560 | B1 | 4/2002 | Chopra et al. |
| 7,923,428 | B2 | 4/2011 | Geffroy et al. |
| 8,889,373 | B2 | 11/2014 | Clendennen |
| 8,900,625 | B2 | 12/2014 | Damaj et al. |
| 9,120,846 | B2 | 9/2015 | Aymore |
| 9,381,147 | B2 | 7/2016 | Fevola et al. |
| 9,993,408 | B2 * | 6/2018 | Fevola ..................... C11D 1/94 |
| 2004/0101505 | A1 | 5/2004 | Payne et al. |
| 2006/0035807 | A1 | 2/2006 | Kasturi et al. |
| 2007/0042030 | A1 | 2/2007 | Cevc |
| 2010/0016198 | A1 | 1/2010 | Bernhardt et al. |
| 2010/0159393 | A1 * | 6/2010 | Fiebag ................... B41C 1/1008 430/302 |
| 2011/0300093 | A1 | 12/2011 | Bendejacq et al. |
| 2012/0277324 | A1 | 11/2012 | Burk et al. |
| 2014/0345483 | A1 | 11/2014 | Imaizumi et al. |
| 2016/0271034 | A1 | 9/2016 | Fevola et al. |

FOREIGN PATENT DOCUMENTS

| CN | 102896879 A | 1/2013 |
| CN | 103 468 228 A | 12/2013 |
| DE | 1 240 872 B | 5/1967 |

(Continued)

OTHER PUBLICATIONS

Morita N-Ethylcarbazole-Containing Amphiphile, Langmuir p. 171 (Year: 1998).*
Huhtanen, J Am Oil Chem Soc p. 854 (Year: 1978).*
T.A. Spencer et al., "Zwitterionic Sulfobetaine Inhibitors of Squalene Synthase," J. Org. Chem., vol. 64, pp. 807-818 (1999).
C.Y. Guo et al., "Synthesis of Surface-Functionalized, Probe-Containing, Polymerized Vesicles Derived from Ammonium Bromide Surfactants," Langmuir, vol. 8, pp. 815-823 (1992).
S. Hashmi et al., "Supramolecular Interaction Controlled Diffusion Mechanism and Improved Mechanical Behavior of Hybrid Hydrogel Systems of Zwitterions and CNT," Macromolecules, vol. 45, pp. 9804-9815 (2012).

(Continued)

Primary Examiner — Matthew P Coughlin
Assistant Examiner — Thurman Wheeler
(74) Attorney, Agent, or Firm — Phan Law Group PLLC

(57) ABSTRACT

Disclosed are a variety of amphoteric compounds containing a quaternary nitrogen group, a covalently bound counterion, and an ester or amide group. These amphoteric compounds can be advantageously prepared via a chemoenzymatic green process, and exhibit good surfactant properties.

9 Claims, No Drawings

(56) References Cited

FOREIGN PATENT DOCUMENTS

| | | |
|---|---|---|
| DE | 2 252 687 A1 | 5/1974 |
| DE | 274332 A3 | 12/1989 |
| DE | 278053 A1 | 4/1990 |
| DE | 278054 A1 | 4/1990 |
| DE | 278061 A1 | 4/1990 |
| EP | 0 205 626 A1 | 12/1986 |
| EP | 0205626 A1 | 12/1986 |
| EP | 2 818 930 A1 | 12/2014 |
| JP | S42 16415 B1 | 9/1967 |
| JP | S42 26523 B1 | 12/1967 |
| JP | S56 141375 A | 11/1981 |
| JP | 6-184934 A | 7/1994 |
| JP | 06184934 A | 7/1994 |
| JP | 7-309724 A | 11/1995 |
| JP | 10-97065 | 4/1998 |
| WO | 98/33879 A1 | 8/1998 |
| WO | 2007/023336 A2 | 3/2007 |
| WO | 2007/059021 A1 | 5/2007 |
| WO | 2009/136396 A2 | 11/2009 |
| WO | WO2010024356 * 3/2010 | ......... A61K 31/4375 |
| WO | 2011/046595 A1 | 4/2011 |
| WO | 2011/114876 A1 | 9/2011 |
| WO | 2011/146595 A2 | 11/2011 |
| WO | 2012/024233 A2 | 2/2012 |
| WO | 2012/061098 A1 | 5/2012 |
| WO | 2012/080018 A2 | 6/2012 |
| WO | 2013/052087 A1 | 4/2013 |
| WO | 2016/064549 A1 | 4/2016 |

OTHER PUBLICATIONS

S. Abele et al., "Cationic and Zwitterionic Polymerizable Surfactants: Quaternary Ammonium Dialkyl Maleates 1. Synthesis and Characterization," Langmuir, vol. 15, pp. 1033-1044 (1999).
H. Liu et al., "Zwitterionic copolymer-based and hydrogen bonding-strengthened self-healing hydrogel," RSC Adv., vol. 5, pp. 33083-33088 (2015).
D. Kratzer et al., "A Synthetic Route to Sulfobetaine Methacrylates with Varying Charge Distance," Eur. J. Org. Chem., vol. 2014, pp. 8064-8071 (2014).
H. Tremblay et al., "One-pot synthesis of polyunsaturated fatty acid amides with anti-proliferative properties," Bioorg. Med. Chem. Lett., vol. 24, pp. 5635-5638 (2014).
N.N. Gandhi, "Applications of Lipase," JAOCS, vol. 74, pp. 621-634 (1997).
Int'l Search Report and Written Opinion issued in Int'l Application No. PCT/US2015/055258.
Boaz et al., Copending U.S. Appl. No. 15/283,739, filed Oct. 3, 2016.
Human English Translation of CN 103 468 228, pp. 1-9 (2013).
"Supplementary Examination Guidelines for Determining Compliance with 35 U.S.C. 112 and for Treatment of Related Issues in Patent Applications," Fed. Reg., vol. 76, No. 27, pp. 7162-7175 and slides 1, 64-67 (2011).
W.M. Wu et al., "Stereoisomers of N-substituted soft anticholinergics and their zwitterionic metabolite based on glycopyrrolate—syntheses and pharmacological evaluations," Pharmazie, vol. 63, pp. 200-209 (2008).
Copending U.S. Appl. No. 14/518,476, filed Oct. 20, 2014.
Copending U.S. Appl. No. 14/518,505, filed Oct. 20, 2014.
Copending U.S. Appl. No. 14/518,517, filed Oct. 20, 2014.
Copending U.S. Appl. No. 14/856,830, filed Sep. 17, 2015.
A. Chattopadhyay et al., "Fluorometric Determination of Critical Micelle Concentration, Avoiding Interference from Detergent Charge," Anal. Biochem., vol. 139, pp. 408-412 (1984).
ASTM D 1173-07, Standard Test Method for Foaming Properties of Surface-Active Agents, pp. 1-3 (2007).
Int'l Search Report issued in Int'l Application No. PCT/US2015/053426.
Int'l Search Report issued in Int'l Application No. PCT/US2015/055263.
Copending U.S. Appl. No. 15/170,097, filed Jun. 1, 2016.
N. Parris et al., "Soap Based Detergent Formulation: XXIV. Sulfobetaine Derivatives of Fatty Amides," J. Am. Oil Chem. Soc., vol. 54, pp. 294-296 (1977).
Int'l Search Report and Written Opinion issued in Int'l Appl. No. PCT/US2016/049972 dated Nov. 16, 2016.
Int'l Search Report and Written Opinion issued in Int'l Appl. No. PCT/US2016/050470 dated Nov. 15, 2016.
C. Tastet et al., "Structure-efficiency relationships of zwitterionic detergents as protein solubilizers in two-dimensional electrophoresis," Proteomics 2003, 3, 111-121.
English machine translation of EP 0 205 626, pp. 1-5 (Dec. 30, 1986).
English machine translation of JP 06-184934, pp. 1-12 (Jul. 5, 1994).
English machine translation of JP0730724, pp. 1-26 (Unknown).
English machine translation of DE 1 240 872 B, pp. 1-8 (May 24, 1967).
Copending U.S. Appl. No. 15/909,653, filed Mar. 1, 2018.

* cited by examiner

AMPHOTERIC COMPOUNDS

PARTIES TO JOINT RESEARCH AGREEMENT

Inventions disclosed or claimed herein were made pursuant to a Joint Research Agreement between Eastman Chemical Company and Johnson & Johnson Consumer Inc.

FIELD OF THE INVENTION

The invention generally relates to amphoteric compounds. More particularly, the invention relates to zwitterionic ammonium compounds containing an ester or amide group, compositions of such compounds, uses of such compounds, and processes for making them.

BACKGROUND OF THE INVENTION

There is an increasing industrial and societal need for safer and more environmentally-friendly ingredients and methods for preparing those ingredients. In particular, it is highly desirable to provide methods that reduce or eliminate the use of irritating or allergenic starting materials, that employ biocompatible reagents, and that optimally use starting materials derived at least in part from a natural source or are "nature-equivalent." This is of urgent interest in consumer-facing industries, such as personal and household care.

One class of materials that may be approached in a "greener" manner is surfactants. Specifically, there is a need for new amphoteric surfactants that avoid using irritating or allergenic starting materials and that are made in a more environmentally-friendly manner.

Amphoteric (or zwitterionic) surfactants are used throughout the personal and household care industries. They are classified as specialty co-surfactants that complement the performance of primary surfactants. These co-surfactants also increase the mildness of the formulation by reducing irritation associated with purely ionic surfactants.

The most common zwitterionic surfactants are amidoamine based materials using a diamine linker between the hydrophobe and the hydrophile, and are produced by a multi-step process from coconut or palm kernel oil and the diamine N,N-dimethylamino-3-propylamine (DMAPA). Various patents (U.S. Pat. Nos. 3,280,179; 4,259,191) and publications (Parris et al., *J. Am. Oil Chem. Soc.*, Vol. 54, pp. 294-296 (1977)) detail commonly used preparation methods for these types of materials. The processes generally involve the amidation of fatty acids with DMAPA at high temperatures (150-175° C.). The intermediate fatty amino-amide is then reacted with a hydrophilic species (e.g., sodium chloroacetate, propane sultone, or sodium 3-chloro-2-hydroxypropanesulfonate) to yield the final zwitterionic surfactant.

These processes have several drawbacks. For example, typical amidation processes require high temperatures for conversion and then distillation to remove unreacted starting materials. These high reaction temperatures can generate by-products and impart color to the products, requiring additional steps to remove the by-products and the color.

Moreover, DMAPA is a known sensitizer, as is the corresponding amido-amine. Both are found in trace quantities in the final formulation.

Thus, there is a need for amphoteric/zwitterionic surfactants that can be prepared under milder conditions without using DMAPA or a DMAPA amide and/or that can retain or improve the performance properties of traditional zwitterionic surfactants.

The present invention addresses this need as well as others, which will become apparent from the following description and the appended claims.

SUMMARY OF THE INVENTION

The invention is as set forth in the appended claims.

Briefly, in one aspect, the present invention provides a compound having the formula 1:

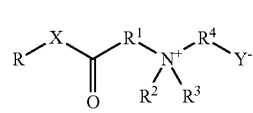

wherein
R is a $C_3$-$C_{24}$ hydrocarbyl group;
$R^1$ is a $C_2$-$C_8$ hydrocarbyl group;
$R^2$ and $R^3$ are each independently a $C_1$-$C_6$ alkyl or alkenyl group;
at least two of $R^1$, $R^2$, and $R^3$ may be connected with the $N^+$ to form a heterocyclic ring;
$R^4$ is a $C_1$-$C_8$ hydrocarbyl group;
X is O or NH; and
$Y^-$ is $CO_2^-$, $SO_3^-$, $SO_4^-$, $PO_3^-$, or $PO_4^-$.

In one embodiment, when R is a $C_6$-$C_{18}$ hydrocarbyl group, $R^1$ is propylene, $R^2$ and $R^3$ are methyl, and $Y^-$ is $CO_2^-$ or $SO_3^-$ in formula 1; $R^4$ is methylene or a substituted hydrocarbyl group.

In another aspect, the present invention provides a mixture comprising at least two compounds having the formula 1. The at least two compounds have at least one different R substituent.

In another aspect, the present invention provides a process for preparing the compound of formula 1. The process comprises:

(a) contacting an amine or alcohol of formula 2 with an amino acid derivative of formula 3:

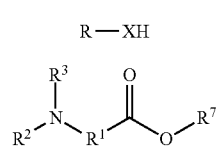

in the presence of an enzyme at conditions effective to form an intermediate of formula 4:

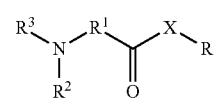

wherein R, $R^1$, $R^2$, $R^3$, and X are as defined above and $R^7$ is hydrogen or a $C_1$-$C_4$ alkyl group; and (b) contacting the intermediate of formula 4 with a carboxylate, sulfonate, or phosphate alkylating agent at conditions effective to form the compound of formula 1.

In yet another aspect, the present invention provides a process for preparing a mixture comprising at least two compounds having the formula 1 wherein the at least two compounds have different R substituents. The process comprises:

(a) contacting a mixture comprising at least two amines or alcohols of formula 2 with an amino acid derivative of formula 3:

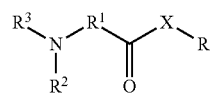

in the presence of an enzyme at conditions effective to form at least two intermediates of formula 4:

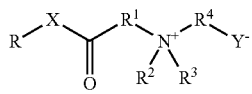

wherein

R, $R^1$, $R^2$, $R^3$, and X are as defined above, $R^7$ is hydrogen or a $C_1$-$C_4$ alkyl group, the at least two amines or alcohols of the formula 2 have different R substituents, and the at least two intermediates of the formula 4 have different R substituents; and (b) contacting the intermediates of formula 4 with a carboxylate, sulfonate, sulfate, phosphonate, or phosphate alkylating agent at conditions effective to form the mixture of at least two compounds of the formula 1.

DETAILED DESCRIPTION OF THE INVENTION

In one aspect, the present invention provides a series of amphoteric compounds having the formula 1:

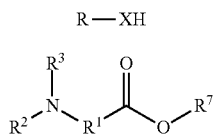

wherein

R is a $C_3$-$C_{24}$ hydrocarbyl group;

$R^1$ is a $C_2$-$C_8$ hydrocarbyl group;

$R^2$ and $R^3$ are each independently a $C_1$-$C_6$ alkyl or alkenyl group;

at least two of $R^1$, $R^2$, and $R^3$ may be connected with the $N^+$ to form a heterocyclic ring;

$R^4$ is a $C_1$-$C_8$ hydrocarbyl group;

X is O or NH; and $Y^-$ is $CO_2^-$, $SO_3^-$, $SO_4^-$, $PO_3^-$, or $PO_4^-$.

In one embodiment, when R is a $C_6$-$C_{18}$ hydrocarbyl group, $R^1$ is propylene, $R^2$ and $R^3$ are methyl, and $Y^-$ is $CO_2^-$ or $SO_3^-$ in formula 1; $R^4$ is methylene or a substituted hydrocarbyl group (preferably, a hydroxy-substituted hydrocarbyl group).

In another embodiment, X is NH.

As used herein, the term "hydrocarbyl" refers to mono- or di-valent hydrocarbon groups, depending on context. The term includes traditional hydrocarbyls such as alkyls, alkenes, alkynes, aryls, and cycloalkyls as well as hydrocarbylenes such as alkylenes, alkenylenes, alkynylenes, arylenes, and cycloalkylenes.

The hydrocarbyl group of R may be branched or straight-chain; and saturated, mono-unsaturated, or poly-unsaturated. The hydrocarbyl group of R may contain up to 24 carbon atoms, such as from 3 to 24 carbon atoms, 3 to 20 carbon atoms, 3 to 16 carbon atoms, 3 to 12 carbon atoms, 3 to 8 carbon atoms, 6 to 24 carbon atoms, 6 to 20 carbon atoms, 6 to 16 carbon atoms, 6 to 12 carbon atoms, or 6 to 8 carbon atoms.

In one embodiment, R is a saturated, mono-unsaturated, or poly-unsaturated hydrocarbyl group derived from a vegetable oil, a nut oil, or a seed oil (e.g., palm oil, soybean oil, peanut oil, olive oil, coconut oil, or palm kernel oil). Preferred examples of oils include coconut oil, hydrogenated coconut oil, palm kernel oil, and hydrogenated palm kernel oil.

The hydrocarbyl group of R may also be a substituted or unsubstituted $C_3$-$C_8$ cycloalkyl group. The term "$C_3$-$C_8$-cycloalkyl" is used to denote a saturated, carbocyclic hydrocarbon radical having three to eight carbon atoms. The $C_3$-$C_8$ cycloalkyl group may be substituted with one to five substituents selected from the group consisting of $C_1$-$C_6$ alkoxy, $C_1$-$C_6$ carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, aryl, heteroaryl, thioether, $C_2$-$C_{10}$ dialkylamino, chlorine, and bromine.

As used herein, the terms "$C_1$-$C_6$ alkoxy," "$C_2$-$C_6$ alkoxycarbonyl," and "$C_2$-$C_6$ alkanoyloxy" are used to denote radicals corresponding to the structures —$OR^5$, —$CO_2R^5$, and —$OCOR^5$, respectively, where $R^5$ is a substituted or unsubstituted $C_1$-$C_6$ alkyl group.

As used herein, the terms "$C_1$-$C_{15}$ aminocarbonyl" and "$C_1$-$C_{15}$ amido" are used to denote radicals corresponding to the structures —$NHCOR^6$ and —$CONHR^6$, respectively, where $R^6$ is a substituted or unsubstituted $C_1$-$C_{15}$ alkyl group.

The divalent hydrocarbyl group of $R^1$ may be branched or straight-chain; and saturated, mono-unsaturated, or poly-unsaturated. The hydrocarbyl group of $R^1$ may contain from 2 to 8 carbon atoms. The hydrocarbyl group of $R^1$ may also be a $C_3$-$C_8$ cycloalkylene group.

The groups represented by $R^2$ and $R^3$ may be substituted or unsubstituted and branched or straight-chain. The alkyl and alkenyl groups represented by $R^2$ and $R^3$ may contain up to six carbon atoms.

$R^2$ and $R^3$ each independently may be substituted with one to three substituents selected from the group consisting of $C_1$-$C_6$ alkoxy, carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, aryl, heteroaryl, thioether, and $C_3$-$C_{15}$ trialkylammonium.

At least two of $R^1$, $R^2$, and $R^3$ may be connected with the $N^+$ to form one or more heterocyclic rings. The resulting heterocycle (with the nitrogen) may be saturated, mono-unsaturated, or poly-unsaturated and may be a mono- or multi-cyclic ring structure. Examples of these heterocyclic structures include pyrrolidinium, piperidinium, pyridinium, quinolinium, tetrahydroquinolinium, indolinium, octahydroindolinium, acridinium, octahydroacridinium, and tetradecahydroacridinium.

The divalent hydrocarbyl radicals represented by $R^4$ may be straight-chain or branched and may be substituted or unsubstituted. The hydrocarbyl group of $R^4$ may contain from 1 to 8 carbon atoms.

The hydrocarbyl group of $R^4$ may be substituted with one to three substituents selected from the group consisting of $C_1$-$C_6$ alkoxy, carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, aryl, heteroaryl, thioether, $C_3$-$C_{15}$ trialkylammonium, chlorine, and bromine.

In one embodiment, $R^4$ is substituted with a hydroxyl group.

Examples of the compounds of the invention include those represented by the formula 1 where R is selected from the group consisting of straight-chain or branched $C_6$-$C_{20}$ alkyl, $C_6$-$C_{18}$ alkenyl, $C_6$-$C_{18}$ dienyl, and substituted or unsubstituted $C_3$-$C_8$ cycloalkyl; $R^1$ is a straight-chain or branched $C_3$-$C_4$ alkylene group; $R^2$ and $R^3$ are each independently selected from the group consisting of $C_1$-$C_6$ alkyl and $C_1$-$C_6$ alkenyl; $R^4$ is selected from the group consisting of methylene, ethylene, propylene, butylene, and hydroxypropylene; X is O or NH; and $Y^-$ is $CO_2^-$ or $SO_3^-$.

Other examples of the compounds of the invention include those represented by the formula 1 where R is selected from the group consisting of straight-chain or branched $C_6$-$C_{20}$ alkyl, $C_6$-$C_{18}$ alkenyl, and $C_6$-$C_{18}$ dienyl; $R^1$ is 1,3-propylene or 1,4-butylene; $R^2$ and $R^3$ are both methyl; $R^4$ is 2-hydroxy-1,3-propylene; X is O or NH; and $Y^-$ is $SO_3^-$.

Additional examples of the compounds of the invention include those represented by the formula 1 where R is lauryl, myristyl, cetyl, stearyl, or a $C_6$ to $C_{20}$ alkyl radical derived from a vegetable oil, a nut oil, or a seed oil; $R^1$ is ethylene, 1,3-propylene, or 1,4-butylene; $R^2$ and $R^3$ are both methyl; $R^4$ is methylene, ethylene, propylene, butylene, or hydroxypropylene; X is O or NH; and $Y^-$ is $CO_2^-$ or $SO_3^-$.

Yet additional examples of the compounds of the invention include those represented by the formula 1 where R is lauryl, myristyl, cetyl, stearyl, or a $C_6$ to $C_{20}$ alkyl radical derived from a vegetable oil, a nut oil, or a seed oil; $R^1$ and $R^2$ combine with the $N^+$ to form a 3-piperidininum, a 4-piperidinium, a 3-piperidiniummethyl, a 4-piperidiniummethyl, a 3-pyridinum, a 4-pyridinum, a 3-pyridiniummethyl, or a 4-pyridiniummethyl group; $R^3$ is methyl; $R^4$ is methylene, ethylene, propylene, butylene, or hydroxypropylene; X is O or NH; and $Y^-$ is $CO_2^-$ or $SO_3^-$.

Yet additional examples of the compounds of the invention include those represented by the formula 1 where R is lauryl, myristyl, or a $C_6$ to $C_{20}$ alkyl radical derived from a vegetable oil, a nut oil, or a seed oil; $R^1$ is 1,3-propylene or 1,4-butylene; $R^2$ and $R^3$ are both methyl; $R^4$ is 2-hydroxy-1,3-propylene; X is O or NH; and $Y^-$ is $SO_3^-$.

Specific examples of the compounds of the formula 1 include (3-lauryloxycarbonylpropyl)dimethylammonioacetate, 3-(3-(lauryloxycarbonylpropyl)dimethylammonio)-2-hydroxypropanesulfonate, 3-(3-(lauryloxycarbonylpropyl) dimethylammonio)propanesulfonate, (4-lauryloxycarbonylbutyl)dimethylammonioacetate, (4-laurylamino-4-oxobutyl)dimethylammonioacetate, (5-laurylamino-5-oxopentyl)dimethylammonioacetate, 3-(5-laurylamino-5-oxopentyl)dimethylammonio) propanesulfonate, 3-(4-(lauryloxycarbonylbutyl)dimethylammonio)-2-hydroxypropanesulfonate, 3-((4-laurylamino-4-oxobutyl)dimethylammonio)-2-hydroxypropanesulfonate, 3-((4-laurylamino-4-oxobutyl)dimethylammonio)propanesulfonate, 3-((4-coconut alkyl amino-4-oxobutyl)dimethylammonio)-2-hydroxypropanesulfonate, 3-((4-stearylamino-4-oxobutyl)dimethylammonio)-2-hydroxypropanesulfonate, 3-((5-laurylamino-5-oxopentyl)dimethylammonio)-2-hydroxypropanesulfonate, 3-((5-coconut alkyl amino-5-oxopentyl)dimethylammonio)-2-hydroxypropanesulfonate, 3-(5-coconut alkyl amino-5-oxopentyl)dimethylammonio) propanesulfonate, and (4-coconut alkyl amino-4-oxobutyl)dimethylammonioacetate.

In one embodiment, the compounds of formula 1 have a solubility of at least 5 wt % in water at 20 to 50° C. In other embodiments, the compounds of formula 1 have a solubility of at least 10, 15, 20, 25, or 30 wt % in water at 20 to 50° C.

In various embodiments of the invention, the "$C_6$ to $C_{20}$ alkyl radical" of R in formula 1 may be derived from coconut oil, hydrogenated coconut oil, hydrogenated and/or fractionated coconut oil fatty acids, palm kernel oil, hydrogenated palm kernel oil, or hydrogenated and/or fractionated palm kernel oil fatty acids. Methods for converting the oils or fatty acids to the corresponding fatty alcohols or fatty amines are known in the art. In such cases, the resulting product may be a mixture of two or more compounds of the formula 1 where each compound has a different R substituent. For example, the "$C_6$ to $C_{20}$ alkyl radical" may be derived from hydrogenated and stripped/fractionated coconut fatty acids. Coconut fatty acids typically include a mixture of fatty acids, such as $C_8$, $C_{10}$, $C_{12}$, $C_{14}$, $C_{16}$, and $C_{18}$ fatty acids. The fatty acids may be saturated, mono-unsaturated, or poly-unsaturated. The mixture may be hydrogenated to increase its melting point. In addition, the mixture may be stripped, for example, of the medium-chain fatty acids, such as $C_8$ and $C_{10}$ fatty acids, to yield a fraction of predominately long-chain fatty acids, such as $C_{12}$-$C_{18}$ fatty acids. These fractions (either the medium-chain or the long-chain, for example) may be used to produce the compounds of the invention. When such fractions are used, the reaction product would include a mixture of the compounds of the formula 1 where some compounds may have, for example, a $C_{12}$ alkyl radical substituent while other compounds may have a $C_{14}$ alkyl radical substituent, etc.

Thus, in another aspect, the present invention provides a mixture comprising at least two compounds having the formula 1:

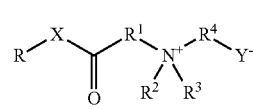

1 wherein

R is a $C_3$-$C_{24}$ hydrocarbyl group;

$R^1$ is a $C_2$-$C_8$ hydrocarbyl group;

$R^2$ and $R^3$ are each independently a $C_1$-$C_6$ alkyl or alkenyl group;

at least two of $R^1$, $R^2$, and $R^3$ may be connected with the $N^+$ to form a heterocyclic ring;

$R^4$ is a $C_1$-$C_8$ hydrocarbyl group;

X is O or NH; and $Y^-$ is $CO_2^-$, $SO_3^-$, $SO_4^-$, $PO_3^-$, or $PO_4^-$. The at least two compounds have at least one different R substituent. In other words, the at least two compounds have different R substituents.

In one embodiment of the mixture, when R is a $C_6$-$C_{18}$ hydrocarbyl group, $R^1$ is propylene, $R^2$ and $R^3$ are methyl, and Y⁻ is $CO_2^-$ or $SO_3^-$ in formula 1; $R^4$ is methylene or a substituted hydrocarbyl group (preferably, a hydroxy substituted hydrocarbyl group).

In another embodiment of the mixture, X is NH.

Examples of mixtures according to the invention include two or more compounds represented by the formula 1 where R is selected from the group consisting of straight-chain or branched $C_6$-$C_{20}$ alkyl, $C_6$-$C_{18}$ alkenyl, $C_6$-$C_{18}$ dienyl, and substituted or unsubstituted $C_3$-$C_8$ cycloalkyl; $R^1$ is a straight-chain or branched $C_3$-$C_4$ alkylene group; $R^2$ and $R^3$ are each independently selected from the group consisting of $C_1$-$C_6$ alkyl and $C_1$-$C_6$ alkenyl; $R^4$ is selected from the group consisting of methylene, ethylene, propylene, butylene, and hydroxypropylene; X is O or NH; and Y⁻ is $CO_2^-$ or $SO_3^-$.

Other examples of mixtures according to the invention include two or more compounds represented by the formula 1 where R is selected from the group consisting of straight-chain or branched $C_6$-$C_{20}$ alkyl, $C_6$-$C_{18}$ alkenyl, and $C_6$-$C_{18}$ dienyl; $R^1$ is 1,3-propylene or 1,4-butylene; $R^2$ and $R^3$ are both methyl; $R^4$ is 2-hydroxy-1,3-propylene; X is O or NH; and Y⁻ is $SO_3^-$.

Additional examples of mixtures according to the invention include two or more compounds represented by the formula 1 where R is lauryl, myristyl, cetyl, stearyl, or a $C_6$ to $C_{20}$ alkyl radical derived from a vegetable oil, a nut oil, or a seed oil; $R^1$ is ethylene, 1,3-propylene, or 1,4-butylene; $R^2$ and $R^3$ are both methyl; $R^4$ is methylene, ethylene, propylene, butylene, or hydroxypropylene; X is O or NH; and Y⁻ is $CO_2^-$ or $SO_3^-$.

Yet additional examples of mixtures according to the invention include two or more compounds represented by the formula 1 where R is lauryl, myristyl, cetyl, stearyl, or a $C_6$ to $C_{20}$ alkyl radical derived from a vegetable oil, a nut oil, or a seed oil; $R^1$ and $R^2$ combine with the N⁺ to form a 3-piperidininum, a 4-piperidinium, a 3-piperidiniummethyl, a 4-piperidiniummethyl, a 3-pyridinum, a 4-pyridinium, a 3-pyridiniummethyl, or a 4-pyridiniummethyl group; $R^3$ is methyl; $R^4$ is methylene, ethylene, propylene, butylene, or hydroxypropylene; X is O or NH; and Y⁻ is $CO_2^-$ or $SO_3^-$.

Yet additional examples of mixtures according to the invention include two or more compounds represented by the formula 1 where R is lauryl, myristyl, or a $C_6$ to $C_{20}$ alkyl radical derived from a vegetable oil, a nut oil, or a seed oil; $R^1$ is 1,3-propylene or 1,4-butylene; $R^2$ and $R^3$ are both methyl; $R^4$ is 2-hydroxy-1,3-propylene; X is O or NH; and Y⁻ is $SO_3^-$.

In another aspect, the present invention provides a process for preparing a compound of the formula 1. The process may be used to prepare any of the compounds of the formula 1 described herein. The process comprises:

(a) contacting an amine or alcohol of formula 2 with an amino acid derivative of formula 3:

R—XH  2

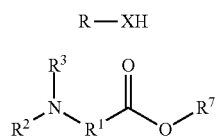
3 in the presence of an enzyme at conditions effective to form an intermediate of formula 4:

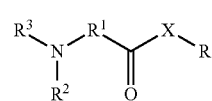
4 wherein R, $R^1$, $R^2$, $R^3$, and X are as defined hereinabove and $R^7$ is hydrogen or a $C_1$-$C_4$ alkyl group; and (b) contacting the intermediate of formula 4 with a carboxylate, sulfonate, or phosphate alkylating agent at conditions effective to form the compound of formula 1.

The $C_1$-$C_4$ alkyl group of $R^7$ may be branched or straight-chain.

The alcohol or amine of the formula 2 may be obtained commercially. Examples of such alcohols and amines include 1-propanol, 2-propanol, 1-butanol, 2-butanol, isobutanol, lauryl alcohol, myristyl alcohol, cetyl alcohol, stearyl alcohol, coconut alcohol, propylamine, isopropylamine, n-butylamine, sec-butylamine, tert-butylamine, isobutylamine, laurylamine, myristylamine, cetylamine, stearylamine, and coconut alkyl amine.

Likewise, the amino acid derivatives of the formula 3 may be obtained commercially or may be produced by methods known in the art, including reacting a haloalkyl ester with a dialkylamine.

The first step of the process involves reacting the amine or alcohol of the formula 2 with the amino acid derivative of the formula 3 in the presence of an enzyme to form the intermediate of the formula 4.

The enzymatic reaction of step (a) may be carried out without an added solvent or in the presence of an inert solvent. Examples of inert solvents include cyclic or acyclic ether solvents (such as diethyl ether, diisopropyl ether, tert-butyl methyl ether, and tetrahydrofuran), aromatic hydrocarbons (such as benzene, toluene, and xylene), aliphatic or alicyclic, saturated or unsaturated hydrocarbons (such as hexane, heptane, cyclohexane, and limonene), halogenated hydrocarbons (such as dichloromethane, dichloroethane, dibromoethane, tetrachloroethylene, and chlorobenzene), polar aprotic solvents (such as acetonitrile, dimethyl formamide, and dimethyl sulfoxide), and mixtures thereof.

In one embodiment, the enzymatic reaction is carried out in the absence of an added solvent.

In another embodiment, the enzymatic reaction is carried out in the presence of one or more aliphatic hydrocarbons as the solvent.

The enzymatic reaction may be carried out at a temperature from about −100° C. to +90° C., preferably from about 20 to 80° C., and more preferably from 50 to 70° C. The amount of the alcohol or amine 2 may be from 0.5 to 20 equivalents, based on the amino acid derivative 3, preferably from 0.7 to 10 equivalents, and more preferably from 0.9 to 1.5 equivalents.

Step (a) in the process of the invention is desirably carried out in the presence of an enzyme effective to react the alcohol or amine 2 with the amino acid derivative 3 to form the intermediate compound of the formula 4. Effective enzymes for this reaction include lipases. Examples of these enzymes include, but are not limited to, Lipase PS (from *Pseudomonas* sp), Lipase PS-C (from *Pseudomonas* sp immobilized on ceramic), Lipase PS-D (from *Pseudomonas* sp immobilized on diatomaceous earth), Lipoprime 50T, Lipozyme TL IM, Novozym 435 (lipase from *Candida antarctica* immobilized on acrylic resin), and *Candida antarctica* lipase B immobilized on a porous fluoropolymer support as described in U.S. Pat. No. 8,889,373. Immobilized enzymes have the advantage of being easily removed from the product and re-used.

The enzymatic reaction may be carried out with or without in situ water or alcohol by-product removal. The water or alcohol by-product can be removed by any known technique, such as chemically via an alcohol or water absorbent (e.g., molecular sieves) or by physical separation (e.g., evaporation). This by-product removal is preferably performed by evaporation, either by purging the reaction mixture with an inert gas such as nitrogen, argon, or helium, or by performing the reaction at reduced pressures, or both, as these conditions can afford >98% conversion of the amino acid derivative 3 to the intermediate 4. The preferred pressure for carrying out the reaction ranges from 1 Torr (133.3 Pa) to ambient pressure, more preferably from 10 Torr (1,333 Pa) to ambient pressure, and most preferably from 20 Torr (2,666 Pa) to ambient pressure. Any organic solvent that is included in this step may or may not be removed along with the alcohol or water, and may assist in azeotropic removal of the alcohol or water. Upon completion of the reaction in step (a), the intermediate 4 of the process may be isolated using methods known to those of skill in the art, e.g., extraction, filtration, distillation, or crystallization.

The second step in the process to generate the final product of the formula 1 involves reacting the intermediate compound of the formula 4 with a carboxylate, sulfonate, sulfate, or phosphonate, or phosphate alkylating agent. Examples of such alkylating agents include sodium chloroacetate, 1,3-propanesultone, 1,4-butanesultone, sodium 2-chloroethanesulfonate, sodium 3-chloro-2-hydroxypropanesulfonate, 1,2-ethylene sulfate, 1,3-propylene sulfate, 3-bromopropanesulfate, sodium chloromethylphosphonate, sodium 3-chloro-2-hydroxypropylphosphate, sodium 2-chloroethylphosphate, sodium 3-chloro-2-propylphosphate, sodium 2-chloroethoxyethylphosphate, sodium 2,3-epoxypropylphosphate, and sodium 4-chlorobutylphosphate.

This step (b) may also be carried out without an added solvent or in the presence of a solvent. Examples of solvents include water, alcohols and diols (such as methanol, ethanol, 1-propanol, 2-propanol, 1-butanol, 2-butanol, isobutanol, tert-butanol, tert-pentanol, ethylene glycol, 1,2-propanediol, and 1,3-propanediol), cyclic or acyclic ethers (such as diethyl ether, diisopropyl ether, tert-butyl methyl ether, and tetrahydrofuran), ether-alcohols (such as 2-methoxyethanol, 1-methoxy-2-propanol, ethylene glycol monobutyl ether, diethylene glycol monoethyl ether, diethylene glycol monopropyl ether, and diethylene glycol monobutyl ether), ketones (such as acetone, methyl ethyl ketone, methyl propyl ketone, methyl isopropyl ketone, and methyl isobutyl ketone), aromatic hydrocarbons (such as benzene, toluene, and xylene), aliphatic or alicyclic, saturated or unsaturated hydrocarbons (such as hexane, heptane, cyclohexane, and limonene), halogenated hydrocarbons (such as dichloromethane, dichloroethane, dibromoethane, tetrachloroethylene, and chlorobenzene), polar aprotic solvents (such as acetonitrile, dimethyl formamide, and dimethyl sulfoxide), and mixtures thereof. The preferred solvents include water, $C_2$-$C_5$ alcohols, ether-alcohols, ketones, and mixtures thereof.

The second step may be carried out at a temperature from about −100° C. to the boiling point of the solvent (if employed). For example, the temperature may be in the range of 25 to 150° C., 50 to 150° C., 50 to 125° C., or 50 to 100° C.

The reaction in the second step may be carried out over a wide range of pressures. For example, the pressure may range from atmospheric to super-atmospheric, e.g., 5 atmospheres or higher.

The amount of alkylating agent used is not particularly limiting. For example, the alkylating agent may be used in an amount ranging from 0.75 to 20 equivalents based on the intermediate 4, preferably from 1 to 10 equivalents, and more preferably from 1 to 1.5 equivalents.

Optionally, a base (in excess of what is needed to neutralize any acid present) is included in the reaction mixture of step (b). If included, the base may be chosen from metal hydroxides, metal carbonates, and metal bicarbonates. Preferred bases include sodium carbonate and sodium bicarbonate. The amount of base used can be from 0 molar equivalents to 1 molar equivalent, based on the intermediate of the formula 4. The preferred amount is a quantity sufficient to keep the reaction mixture slightly basic, generally a pH of 7.2 or greater.

Upon completion of the reaction in step (b), the product 1 may be isolated using methods known to those of skill in the art, e.g., extraction, filtration, or crystallization.

The process of the invention may be used to prepare a mixture of two or more compounds of the formula 1. In particular, the process may be used to prepare any mixture of two or more compounds of the formula 1 described herein. As noted above, the two or more compounds of the formula 1 would have different R substituents. If desired, a mixture of two or more alcohols or amines of the formula 2, with different R substituents, may be employed in the enzymatic reaction step (a). Such mixtures may be derived from, for example, coconut oil, hydrogenated coconut oil, hydrogenated and/or fractionated coconut oil fatty acids, palm kernel oil, hydrogenated palm kernel oil, or hydrogenated and/or fractionated palm kernel oil fatty acids. The enzymatic reaction step (a) would yield a mixture of two or more intermediates of the formula 4, wherein the intermediates 4 would have different R substituents. The mixture of intermediates 4 may then be reacted with the alkylating agent to produce the mixture of two or more compounds of the formula 1.

The amphoteric compounds of the formula 1 are particularly useful as surfactants. Thus, another aspect of the present invention relates to compositions of matter comprising one or more compounds of the formula 1 as surfactants. The compositions may contain from 0.001 to 20 weight percent of the compounds of the formula 1.

In particular, the amphoteric compounds of the invention possess both hydrophilic and hydrophobic regions, making them useful as surfactants in a number of formulated product applications, including personal care products, such as skin care, hair care, and other cosmetic products; household and industrial surface cleaners; laundry products; dish cleaners; disinfectants; metal working compositions; rust inhibitors; lubricants; oil field products; oil dispersants; agrochemicals; and dye dispersions. The amphoteric compounds can also be used as emulsifiers and thickening agents in emulsions. The amphoteric compounds can be formulated into products as primary or secondary surface-active agents. Although their primary use is as cleansing and foaming agents, the amphoteric compounds can also be used for their anti-static, viscosity-controlling, emulsifying, wetting, and dispersing properties.

Such formulated products can contain from about 0.001 weight % to about 20 weight %, from about 0.01 weight % to about 15 weight %, or even from about 0.1 weight % to about 10 weight % of the amphoteric compounds.

The formulated products of the invention may include other surfactants in addition to the amphoteric compounds. These other surfactants can include anionic surfactants (such as alcohol ether sulfates, linear alkylbenzene sulfonates, and acyl isethionates), cationic surfactants (such as quaternary ammonium salts, amine oxides, and ester quats), amphoteric surfactants (such as betaines, amidobetaines, ester betaines, and amphoacetates), and non-ionic surfactants (such as alky polyglycosides, alcohol ethoxylates, and fatty alkanol amides). Such ingredients are known to those of skill in the art.

As noted, the formulated products of the invention can be cosmetic, skin, and hair care compositions. Those compositions may contain skin conditioning ingredients or cosmetically acceptable carriers in addition to the amphoteric compounds.

Such skin care ingredients/carriers include retinol, retinyl esters, tetronic acid, tetronic acid derivatives, hydroquinone, kojic acid, gallic acid, arbutin, α-hydroxy acids, niacinamide, pyridoxine, ascorbic acid, vitamin E and derivatives, aloe, salicylic acid, benzoyl peroxide, witch hazel, caffeine, zinc pyrithione, and fatty acid esters of ascorbic acid. Other skin care ingredients and carriers are known to those of skill in the art and may be used in the compositions of the invention.

Additional ingredients that may be included in these formulations include conditioning agents (such as polyquaterniums and panthenol), pearlizing agents (such as glycol distearate, distearyl ether, and mica), UV filters (such as octocrylene, octyl methoxycinnamate, benzophenone-4, titanium dioxide, and zinc oxide), exfoliation additives (such as apricot seeds, walnut shells, polymer beads, and pumice), silicones (such as dimethicone, cyclomethicone, and amodimethicone), moisturizing agents (such as petrolatum, sunflower oil, fatty alcohols, and shea butter), foam stabilizers (such as cocamide MEA and cocamide DEA), anti-bacterial agents such as triclosan, humectants such as glycerin, thickening agents (such as guar, sodium chloride, and carbomer), hair and skin damage repair agents (such as proteins, hydrolyzed proteins, and hydrolyzed collagen), foam boosters such as cocamide MIPA, preservatives (such as phenoyethanol, ethylhexyl glycerin, sodium benzoate, and formaldehyde donors), and fragrances. Such additional ingredients are known to those of skill in the art and may be used in the compositions of the invention.

Many personal care preparations are known in the art. They typically include acceptable carriers (such as water, oils and/or alcohols), emollients (such as olive oil, hydrocarbon oils and waxes, silicone oils, other vegetable, animal or marine fats or oils, glyceride derivatives, fatty acids or fatty acid esters), alcohols or alcohol ethers, lecithin, lanolin and derivatives, polyhydric alcohols or esters, wax esters, sterols, phospholipids, and the like. These same general ingredients can be formulated into liquids (such as liquid soaps, shampoos, or body washes), creams, lotions, gels, or into solid sticks by using different proportions of the ingredients and/or by inclusion of thickening agents such as gums or other forms of hydrophilic colloids. All such preparations may include the amphoteric compounds of the invention.

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention.

EXAMPLES

Example 1

Preparation of Ethyl 4-Dimethylaminobutyrate 40 wt % Dimethylamine in water (266 g; 299 mL; 2.36 mol; 2.5 equiv) was added to DMSO (430 mL) in a 2-L 3-neck flask. The initial heat of the solution (exotherm to 28.4° C.) was cooled to 20° C. with a cold-water bath.

Ethyl 4-bromobutyrate (184 g; 0.943 mol) was placed into a 125-mL addition funnel and washed into the funnel with 15 mL of DMSO. The funnel was placed on top of the flask. Approximately 10 wt % of the mixture was added, resulting in an exotherm. The exotherm was cooled to 21° C. by the addition of ice to the bath, and slow addition of the ethyl 4-bromobutyrate was started such that the temperature remained below 23° C. The total addition time was 45 min.

After the addition was completed, the contents of the addition funnel were washed into the flask with 15 mL of DMSO, and the reaction was stirred at about 20° C. for 1.5 hours, at which point NMR analysis showed the absence of ethyl 4-bromobutyrate.

The reaction mixture was transferred to a separatory funnel with 500 mL of ethyl acetate, and the layers were separated. The bottom layer was extracted with a second portion (250 mL) of ethyl acetate. The combined ethyl acetate solutions were washed twice with water (350 mL and 250 mL), dried with magnesium sulfate, filtered and concentrated to afford 115.53 g of ethyl 4-dimethylaminobutyrate (77% yield).

$^1$H NMR (500 MHz, CDCl$_3$) δ 4.13 (q, 2H); 2.33 (t, 2H); 2.28 (t, 2H); 2.21 (s. 6H); 1.79 (m(5), 2H); 1.25 (s, 3H).

Example 2

Preparation of Lauryl 4-Dimethylaminobutyrate

Ethyl 4-dimethylaminobutyrate (9.00 g; 56.5 mmol), lauryl alcohol (10.80 g; 57.9 mmol; 1.025 equiv), and Novozym 435 (0.50 g) were combined in a 250-mL 3-neck flask with a Dean-Stark trap. 10 mL of heptane was added. The reaction mixture was heated in a 70° C. bath and the pressure was reduced until a good overhead flow of the heptane/ethanol azeotrope was obtained (ca. 100 mm Hg). After 10 h, 99.9% conversion to product was observed according to NMR analysis.

The reaction mixture was filtered to remove the enzyme, the enzyme was washed with heptane, and the combined filtrate was concentrated to afford 16.85 g of product. $^1$H NMR indicated the product contained 96.1 wt % of lauryl 4-dimethylaminobutyrate (96% yield).

$^1$H NMR (500 MHz, CDCl$_3$) δ 4.06 (t, 2H); 2.33 (t, 2H); 2.28 (t, 2H); 2.21 (s, 6H); 1.79 (m, 2H); 1.61 (m, 2H); 1.26 (m, 18H); 0.88 (t, 3H).

HPLC (150×4.6 mm Zorbax SB-C8 column, 80:20 (v:v) methanol:water (containing 0.1 vol % trifluoroacetic acid) for 10 min, gradient to 100% methanol over 1 min, held at 100% methanol for 9 min, ELSD detection): $t_R$ 3.8 min.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, ELSD detection): $t_R$ 6.2 min.

Example 3

Preparation of (3-Lauryloxycarbonylpropyl)dimethylammonioacetate

Lauryl 4-dimethylaminobutyrate (4.00 g; 13.4 mmol), sodium chloroacetate (1.71 g; 14.7 mmol; 1.1 equiv), and sodium bicarbonate (224 mg; 2.7 mmol; 0.2 equiv) were combined with 10.0 g of water in a 100 mL flask and heated to 80° C. After 16 h, 99.8% conversion to product was observed by HPLC analysis.

The reaction mixture was dissolved in isopropanol, and the salts were removed by filtration. The filtrate was concentrated, then diluted with sufficient isopropyl alcohol to afford a flowable solution. $^1$H NMR was consistent with the product structure and indicated 78 wt % of product and 22 wt % of isopropanol.

HPLC (150×4.6 mm Zorbax SB-C8 column, 80:20 (v:v) methanol:water (containing 0.1% trifluoroacetic acid) for 10 min, gradient to 100% methanol over 1 min, held at 100% methanol for 9 min, ELSD detection): $t_R$ 4.6 min.

Example 4

Preparation of 3-(3-(Lauryloxycarbonylpropyl)dimethylammonio)-2-hydroxypropanesulfonate Lauryl 4-dimethylaminobutyrate (3.00 g; 10.0 mmol), sodium 3-chloro-2-hydroxypropanesulfonate (95%, 2.41 g; 11.6 mmol; 1.16 equiv), and sodium carbonate (106 mg; 1.0 mmol; 0.1 equiv) were combined with 9 mL of isopropanol and 2 mL of water in a 100 mL flask and heated to 80° C. for 24 hours to afford 99.2% conversion to product according to HPLC analysis.

Methyl isobutyl ketone (9 mL) was added and the mixture was concentrated to small volume. MIBK (5 mL) was added and the mixture was concentrated once more. Acetone (15 mL) was added, the mixture was briefly heated to reflux, and then allowed to stir at room temperature for 5 h.

The precipitate was collected by filtration, washed with acetone, and air-dried to afford 4.48 g of white solid. $^1$H NMR was consistent with the product structure.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, ELSD detection): $t_R$ 6.8 min.

Example 5

Preparation of 3-(3-(Lauryloxycarbonylpropyl)dimethylammonio)-propanesulfonate 1,3-Propanesultone (1.70 g; 13.92 mmol; 1.0 equiv) was weighed into a 100-mL round bottom flask. Lauryl 4-dimethylaminobutyrate (4.34 g; 13.92 mmol) was dissolved in 21 mL of acetone and added to the flask. The reaction mixture was heated to reflux for 12 hours to afford 97.0% conversion to product according to HPLC analysis.

The reaction mixture was cooled to room temperature. The precipitate was collected by filtration, washed with acetone, and air-dried to afford 5.35 g (91% yield) of 3-(3-(lauryloxycarbonylpropyl)dimethylammonio)-propanesulfonate as a white solid with >99.9% purity according to HPLC analysis. $^1$H NMR was consistent with the product structure.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, ELSD detection): $t_R$ 6.4 min.

Example 6

Preparation of Lauryl 5-Bromovalerate

Lauryl alcohol (25 g; 134 mmol) and 5-bromovaleric acid (24.77 g; 137 mmol; 1.02 equiv) were combined with 1.25 g of Novozym 435. The mixture was heated to 50° C. and sparged with nitrogen (500 mL/min) for 3 h, at which point GC analysis indicated >99% conversion to product. The reaction was stopped after 6 h. The mixture was cooled to ambient temperature and filtered to afford 36.63 g (78% yield) of lauryl 5-bromovalerate.

$^1$H NMR (300 MHz, CDCl$_3$) δ 4.07 (t, 2H); 3.42 (t, 2H); 2.34 (t, 2H); 1.9 (m, 2H); 1.8 (m, 2H); 1.6 (m, 2H); 1.26 (m, 18H); 0.88 (t, 3H).

GC (30 m×0.25 mm DB-5, 100° C. for 10 min, 100-250° C. at 25°/min, 250° C. for 29 min): $t_R$ 24.7 min.

Example 7

Preparation of Lauryl 5-Dimethylaminovalerate

Lauryl 5-bromovalerate (10.37 g; 29.7 mmol) was dissolved in 40 mL of isopropanol and 40% dimethylamine (18.8 mL; 16.73 g; 148 mmol; 5 equiv) was added. The mixture was heated to 50° C. for 10 h to afford >99% conversion to product according to GC analysis with >99% selectivity according to HPLC analysis The mixture was diluted with ethyl acetate (60 mL) and 5% sodium bicarbonate (50 mL), and the layers were mixed and separated. The aqueous layer was extracted with ethyl acetate (40 mL), and the combined ethyl acetate solution was concentrated. The residue was diluted with ethyl acetate, dried with magnesium sulfate, and concentrated to afford 8.98 g (96% yield) of lauryl 5-dimethylaminovalerate.

$^1$H NMR (300 MHz, CDCl$_3$) δ 4.06 (t, 2H); 2.36 (t, 2H); 2.33 (t, 2H); 2.28 (s, 6H); 1.6 (m, 6H); 1.8 (m, 2H); 1.6 (m,

2H); 1.26 (m, 18H); 0.88 (t, 3H). GC (30 m×0.25 mm DB-5, 100° C. for 10 min, 100-250° C. at 25°/min, 250° C. for 29 min): $t_R$ 23.2 min.

HPLC (150×4.6 mm Zorbax SB-C8 column, 80:20 (v:v) methanol:water (containing 0.1% trifluoroacetic acid) for 10 min, gradient to 100% methanol over 1 min, held at 100% methanol for 9 min, ELSD detection): $t_R$ 3.7 min.

Example 8

Preparation of (4-Lauryloxycarbonylbutyl)dimethylammonioacetate

Lauryl 5-dimethylaminovalerate (4.69 g; 13.9 mmol), sodium chloroacetate (1.79 g; 15.3 mmol; 1.1 equiv), and sodium bicarbonate (234 mg; 2.9 mmol; 0.2 equiv) were combined with 10.6 g of water and heated to 80° C. for 17 h, at which point HPLC analysis indicated 95% conversion to product.

Additional sodium chloroacetate (0.18 g; 1.5 mmol; 0.11 equiv) was added, and the mixture was heated to 80° C. for an additional 18 h, at which point HPLC analysis indicated 98% conversion to product.

The reaction mixture was dissolved in isopropanol, and the salts were removed by filtration. The filtrate was concentrated, then diluted with sufficient isopropyl alcohol to afford a flowable solution. $^1$H NMR analysis was consistent with the product structure and indicated 80 wt % of (4-lauryloxycarbonylbutyl)dimethylammonioacetate and 20 wt % of isopropanol.

HPLC (150×4.6 mm Zorbax SB-C8 column, 80:20 (v:v) methanol:water (containing 0.1% trifluoroacetic acid) for 10 min, gradient to 100% methanol over 1 min, held at 100% methanol for 9 min, ELSD detection): $t_R$ 5.0 min.

Example 9

Preparation of 3-(4-(Lauryloxycarbonylbutyl)dimethylammonio)-2-hydroxypropanesulfonate Lauryl 4-dimethylaminovalerate (5.00 g; 15.95 mmol), sodium 3-chloro-2-hydroxypropanesulfonate (95%, 3.63 g; 17.54 mmol; 1.1 equiv), and sodium carbonate (169 mg; 1.6 mmol; 0.1 equiv) were combined with 15 mL of isopropanol and 3.33 mL of water, and heated to 80° C. for 23 hours to afford 99.8% conversion to product according to HPLC analysis.

The reaction mixture was cooled to ambient temperature and filtered to remove salts. The filter cake was washed with isopropanol, and the combined filtrate was concentrated at reduced pressure and then in vacuo to afford 7.69 g of 3-(4-(lauryloxycarbonylbutyl)dimethylammonio)-2-hydroxypropanesulfonate as a white solid. $^1$H NMR was consistent with the product structure.

HPLC (150×4.6 mm Zorbax SB-C8 column, 80:20 (v:v) methanol:water (containing 0.1% trifluoroacetic acid) for 10 min, gradient to 100% methanol over 1 min, held at 100% methanol for 9 min, ELSD detection): $t_R$ 4.8 min.

Example 10

Preparation of Lauryl 4-Dimethylaminobutyramide

Ethyl 4-dimethylaminobutyrate (10 g; 62.8 mmol), laurylamine (11.64 g; 62.8 mmol; 1.0 equiv), and Novozym 435 (1.0 g) were combined and heated overnight at 65° C. with a nitrogen sparge. The mixture was filtered and the enzyme was washed with heptane. The filtrate was concentrated to afford lauryl 4-dimethylaminobutyramide (17.69 g; 94% yield).

$^1$H NMR (300 MHz, CDCl$_3$) δ 6.48 (br s, 1H); 3.22 (q, 2H); 2.30 (t, 2H); 2.24 (t, 2H); 2.20 (s, 6H); 1.78 (t, 2H); 1.48 (m, 2H); 1.26 (s, 18H); 0.88 (t, 3H).

HPLC (150×4.6 mm Zorbax SB-C8 column, 80:20 (v:v) methanol:water (containing 0.1% trifluoroacetic acid) for 10 min, gradient to 100% methanol over 1 min, held at 100% methanol for 9 min, ELSD detection): $t_R$ 3.2 min.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, ELSD detection): $t_R$ 5.0 min.

Example 11

Preparation of (4-Laurylamino-4-oxobutyl)dimethylammonioacetate

Lauryl 4-dimethylaminobutyramide (0.76 g; 2.5 mmol), sodium chloroacetate (0.33 g; 2.8 mmol; 1.1 equiv), and sodium bicarbonate (42 mg; 0.5 mmol; 0.2 equiv) were combined with 1.9 g of water in a vial and heated to 80° C. for 8 h, at which point HPLC analysis indicated >99.5% conversion to product. Cooling to ambient temperature afforded a very thick liquid.

The mixture was diluted with 0.475 mL of water, heated to homogeneity to afford a very flowable solution. $^1$H NMR was consistent with product structure.

HPLC (150×4.6 mm Zorbax SB-C8 column, 80:20 methanol:water (containing 0.1% trifluoroacetic acid) for 10 min, gradient to 100% methanol over 1 min, held at 100% methanol for 9 min, ELSD detection): $t_R$ 3.9 min.

Example 12

Preparation of 3-((4-Laurylamino-4-oxobutyl)dimethylammonio)-2-hydroxy-propanesulfonate Water Solution Lauryl 4-dimethylaminobutyramide (12.5 g; 41.9 mmol), sodium 3-chloro-2-hydroxypropanesulfonate (95%, 9.15 g; 44.2 mmol; 1.06 equiv), and sodium carbonate (444 mg; 4.2 mmol; 0.1 equiv) were combined with 38.8 g of water and heated to 90° C. for 10 hours to afford 99.7% conversion to product according to HPLC analysis. The mixture was cooled to ambient temperature to afford 59.5 g of a very flowable solution.

The material was diluted with a little water and filtered through fine filter paper to afford a solution which analyzed at 24.9 wt % 3-((4-laurylamino-4-oxobutyl)dimethylammonio)-2-hydroxy-propanesulfonate. $^1$H NMR was consistent with the product structure.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, ELSD detection): $t_R$ 5.4 min.

Example 13

Preparation of 3-((4-Laurylamino-4-oxobutyl)dimethylammonio)-2-hydroxy-propanesulfonate Lauryl 4-dimethylaminobutyramide (10.0 g; 33.5 mmol), sodium 3-chloro-2-hydroxypropanesulfonate (95%, 7.28 g; 35.2 mmol; 1.05 equiv), and sodium carbonate (355 mg;

3.35 mmol; 0.1 equiv) were combined with 38 mL of ipa and 5 mL of water. The mixture was heated in an 85° C. oil bath for 12 hours to afford 99.9% conversion to product according to HPLC analysis.

The mixture was cooled to ambient temperature and concentrated at reduced pressure. The residue was combined with 30 mL of methyl isobutyl ketone, and the mixture was concentrated at reduced pressure to small volume. 30 mL of MIBK was added, the mixture was stirred at room temperature for 30 min, and the resulting solid was collected by filtration. The cake was washed with acetone and air-dried to afford 17.48 g of white solid. $^1$H NMR was consistent with the product structure.

Example 14

Preparation of 3-((4-Laurylamino-4-oxobutyl)dimethylammonio)-propanesulfonate 1,3-Propanesultone (152 g; 1.24 mol; 1.0 equiv) was weighed into a 4 L jacketed reactor. Lauryl 4-dimethylaminobutyramide (391 g; 1.24 mol) was dissolved in 2 L of acetone and added to the flask. The reaction mixture was heated to reflux for 18 hours to afford 99.1% conversion to product according to HPLC analysis. The reaction mixture was cooled to room temperature.

The precipitate was collected by filtration, washed with acetone, and air dried to afford 507 g (97%) of 3-((4-laurylamino-4-oxobutyl)dimethyl-ammonio)propane-sulfonate as a white solid with >99.9% purity according to HPLC analysis. $^1$H NMR was consistent with the product structure.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, 220 nm detection): $t_R$ 5.4 min.

Example 15

Preparation of Coconut Alkyl 4-Dimethylaminobutyramide

Ethyl 4-dimethylaminobutyrate (20 g; 126 mmol), coconut alkyl amine (24.57 g; 124 mmol; 0.99 equiv), and Novozym 435 (1.0 g) were combined and heated for 17 h in a 70° C. oil bath with a 50 mL/min headspace nitrogen purge. $^1$H NMR analysis indicated 98% conversion to product. The mixture was heated for an additional 7 h with a 500 mL/min headspace nitrogen purge to afford >99.5% conversion of both components to product according to $^1$H NMR analysis.

The mixture was diluted with heptane (26 mL) and filtered to remove the enzyme. The enzyme was washed with heptane (2×26 mL), and the filtrate was concentrated to afford coconut alkyl 4-dimethylaminobutyramide (38.35 g; 97% yield).

$^1$H NMR (500 MHz, CDCl$_3$) δ 6.43 (br s, 1H); 3.21 (q, 2H); 2.30 (t, 2H); 2.24 (t, 2H); 2.22 (s, 6H); 1.78 (t, 2H); 1.48 (m, 2H); 1.26 (s); 0.88 (t, 3H).

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, 220 nm detection): $t_R$ 4.6 min. (lauramide).

Example 16

Preparation of (4-Coconut alkyl amino-4-oxobutyl)dimethylammonioacetate

Coconut alkyl 4-dimethylaminobutyramide (104 g; 0.335 mol), sodium chloroacetate (42.9 g; 0.368 mol; 1.1 equiv), and sodium bicarbonate (5.62 g; 0.067 mol; 0.2 equiv) were combined with 249 mL of water in a 1-L reactor and heated overnight at 80° C. to afford 99.6% conversion to product according to HPLC analysis. The reaction mixture was filtered and the solution was analyzed by NMR to indicate 28 wt % (4-coconut alkyl amino-4-oxobutyl)dimethylammonioacetate in water.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, 220 nm detection): $t_R$ 4.9 min. (lauramide).

Example 17

Preparation of 3-((4-Coconut alkyl amino-4-oxobutyl)dimethylammonio)-2-hydroxypropanesulfonate Coconut alkyl 4-dimethylaminobutyramide (5.00 g; 16.1 mmol), sodium 3-chloro-2-hydroxypropanesulfonate (95%, 3.50 g; 16.9 mmol; 1.05 equiv), and sodium carbonate (171 mg; 1.61 mmol; 0.1 equiv) were combined with 14.64 g of water in a 100 mL flask and heated to 88-90° C. internal for 8 hours to afford 99.1% conversion to product according to HPLC analysis.

The mixture was cooled to ambient temperature to afford 21.06 g of an approximately 34.0 wt % water solution of 3-((4-coconut alkyl amino-4-oxobutyl)dimethylammonio)-2-hydroxypropanesulfonate. $^1$H NMR was consistent with the product structure.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, 220 nm detection): $t_R$ 5.2 min. (lauramide).

Example 18

Preparation of Ethyl 5-Dimethylaminovalerate

Ethyl 5-bromovalerate (25 g; 120 mmol) was combined with 45 mL of isopropanol and 40% dimethylamine in water (45.4 mL; 40.4 g; 359 mmol; 3 equiv) was added to afford a homogeneous solution. The mixture was stirred vigorously and heated to 50° C. for 2.5 h, at which point GC analysis indicated that the bromo-ester had been completely consumed.

The mixture was cooled to ambient temperature, diluted with 150 mL of ethyl acetate, and washed three times with water (100 mL, 100 mL, and 50 mL). The resulting ethyl acetate solution was dried with magnesium sulfate and concentrated to afford 16.02 g (76% yield) of ethyl 5-dimethylaminovalerate.

$^1$H NMR (300 MHz, CDCl$_3$) δ 4.13 (q, 2H); 2.32 (t, 2H); 2.26 (t, 2H); 2.21 (s. 6H); 1.65 (m, 2H); 1.49 (m, 2H); 1.25 (s, 3H).

GC (30 m×0.25 mm DB-5, 100° C. for 10 min, 100-250° C. at 25°/min, 250° C. for 29 min): $t_R$ 12.6 min.

Example 19

Preparation of Lauryl 5-Dimethylaminovaleramide

Ethyl 5-dimethylaminovalerate (5 g; 28.9 mmol), laurylamine (5.35 g; 28.9 mmol; 1.0 equiv) and Novozym 435 (0.25 g) were combined and heated overnight at 65° C. with a nitrogen headspace purge of 50 mL/min. Analysis indicated no residual ester but 1.3% amine remaining. 50 μL of ethyl 5-dimethylaminovalerate was added, and the mixture was heated at 65° C. with a nitrogen headspace purge of 50 mL/min for 3 h to afford 99.7% conversion to product (based on amine) by $^1$H NMR analysis.

The mixture was diluted with heptane (15 mL), filtered and the enzyme was washed with heptane. The filtrate was concentrated to afford lauryl 5-dimethylaminovaleramide (8.26 g; 92% yield).

$^1$H NMR (500 MHz, CDCl$_3$) δ 5.71 (br s, 1H); 3.22 (q, 2H); 2.27 (t, 2H); 2.21 (s, 6H); 2.19 (t, 2H); 1.66 (m, 2H); 1.49 (m, 4H); 1.26 (s, 18H); 0.88 (t, 3H).

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, 220 nm detection): $t_R$ 4.6 min.

HPLC (150×4.6 mm Zorbax SB-C8 column, 80:20 (v:v) methanol:water (containing 0.1% trifluoroacetic acid) for 10 min, gradient to 100% methanol over 1 min, held at 100% methanol for 9 min, ELSD detection): $t_R$ 3.3 min.

Example 20

Preparation of (5-Laurylamino-5-oxopentyl)dimethylammonioacetate

Lauryl 5-dimethylaminovaleramide (5.00 g; 16.0 mmol), sodium chloroacetate (2.05 g; 17.6 mmol; 1.1 equiv), and sodium bicarbonate (269 mg; 3.2 mmol; 0.2 equiv) were combined with 12.44 g of water in a 100 mL flask and heated to 80° C. for 8 h, at which point HPLC analysis indicated >99.5% conversion to product. Cooling to ambient temperature afforded a solid mass.

The mixture was diluted with sufficient water to afford an approximately 25 wt % solution of (5-laurylamino-5-oxopentyl)dimethylammonioacetate, heated briefly to near reflux, then stirred overnight to afford a clear water solution of (5-laurylamino-5-oxopentyl)dimethylammonioacetate. $^1$H NMR was consistent with the product structure.

HPLC (150×4.6 mm Zorbax SB-C8 column, 80:20 (v:v) methanol:water (containing 0.1% trifluoroacetic acid) for 10 min, gradient to 100% methanol over 1 min, held at 100% methanol for 9 min, ELSD detection): $t_R$ 3.9 min.

Example 21

Preparation of 3-((5-Laurylamino-5-oxopentyl)dimethylammonio)-2-hydroxypropanesulfonate Lauryl 5-dimethylaminovaleramide (5.00 g; 16.0 mmol), sodium 3-chloro-2-hydroxypropanesulfonate (95%, 3.48 g; 16.8 mmol; 1.05 equiv), and sodium carbonate (170 mg; 1.6 mmol; 0.1 equiv) were combined with 15.1 g of water and heated to 90° C. for 12 hours to afford 98.7% conversion to product according to HPLC analysis. The mixture was cooled to ambient temperature to afford 22.0 g of an approximately 32.4 wt % water solution of 3-((5-laurylamino-5-oxopentyl)dimethylammonio)-2-hydroxypropanesulfonate. $^1$H NMR was consistent with the product structure.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, 220 nm detection): $t_R$ 5.3 min.

Example 22

Preparation of 3-((5-Laurylamino-5-oxopentyl)dimethylammonio)-propanesulfonate Lauryl 5-dimethylaminovaleramide (1.50 g; 4.80 mmol) and 1,3-propanesultone (0.616 g; 5.04 mmol; 1.05 equiv) were dissolved in 10 mL of acetone. The reaction mixture was heated to reflux for 18 hours to afford >99% conversion to product according to HPLC analysis. The reaction mixture was cooled to room temperature.

The precipitate was collected by filtration, washed with acetone, and air dried to afford 1.983 g (95% yield) of 3-((4-laurylamino-5-oxopentyl)dimethyl-ammonio)propanesulfonate as a white solid with >99.9% purity according to HPLC analysis. $^1$H NMR was consistent with the product structure.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, 220 nm detection): $t_R$ 5.6 min

Example 23

Preparation of Coconut Alkyl 5-Dimethylaminovaleramide

Ethyl 5-dimethylaminovalerate (5 g; 28.9 mmol), coconut alkyl amine (5.66 g; 28.3 mmol; 0.98 equiv), and Novozym 435 (0.25 g) were combined and heated for 14 hours at 65° C. with a nitrogen headspace purge of 50 mL/min. Analysis by $^1$H NMR indicated 99.7% conversion to product. The mixture was diluted with heptane (10 mL), filtered to remove enzyme, and the enzyme was washed with heptane. The combined filtrate was concentrated to afford coconut alkyl 5-dimethylaminovaleramide (9.12 g; 97% yield) as a low-melting solid, mp 37-39° C.

$^1$H NMR (500 MHz, CDCl$_3$) δ 5.70 (br s, 1H); 3.22 (q, 2H); 2.27 (t, 2H); 2.21 (s, 6H); 2.19 (t, 2H); 1.66 (m, 2H); 1.49 (m, 4H); 1.26 (s); 0.88 (t, 3H).

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, 220 nm detection): $t_R$ 4.6 min. (lauramide).

Example 24

Preparation of 3-((5-Coconut alkyl amino-5-oxopentyl)dimethylammonio)-2-hydroxypropanesulfonate Coconut alkyl 5-dimethylaminovaleramide (5.00 g; 15.3 mmol), sodium 3-chloro-2-hydroxypropanesulfonate (95%, 3.32 g; 16.1 mmol; 1.05 equiv), and sodium carbonate (162 mg; 1.53 mmol; 0.1 equiv) were combined with 14.99 g of water in a 100 mL flask and heated in a 90° C. oil bath for 12 hours to afford 99.0% conversion to product according to HPLC analysis. The mixture was cooled to ambient temperature to afford 21.95 g of an approximately 32.1 wt % water solution of 3-((5-coconut alkyl amino-5-oxopentyl) dimethylammonio)-2-hydroxypropanesulfonate. $^1$H NMR was consistent with the product structure.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, 220 nm detection): $t_R$ 5.3 min. (lauramide).

Example 25

Preparation of 3-((5-Coconut alkyl amino-5-oxopentyl)dimethylammonio)-propanesulfonate Coconut alkyl 5-dimethylaminovaleramide (1.50 g; 4.58 mmol) and 1,3-propanesultone (0.616 g; 5.04 mmol; 1.10 equiv) were dissolved in 10 mL of acetone. The reaction mixture was heated to reflux for 18 hours to afford >99% conversion to product according to HPLC analysis. The reaction mixture was cooled to room temperature.

The precipitate was collected by filtration, washed with acetone, and air dried to afford 1.961 g (95% yield) of 3-((4-coconut alkyl amino-5-oxopentyl)dimethyl-ammonio) propanesulfonate as a white solid with >99.9% purity according to HPLC analysis. $^1$H NMR was consistent with the product structure.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, 220 nm detection): $t_R$ 5.6 min (lauramide).

Example 26

Preparation of Stearyl 4-Dimethylaminobutyramide

Ethyl 4-dimethylaminobutyrate (20 g; 126 mmol), stearylamine (33.9 g; 126 mmol; 1.0 equiv), and Novozym 435 (1.0 g) were combined and heated in a 70° C. oil bath with a headspace nitrogen purge (100 mL/min). After 23 h, NMR analysis shows complete conversion of both reactants to product. The mixture was diluted with 120 mL of heptane, heated, filtered to remove the enzyme, and the enzyme was washed with heptane. Upon cooling, the product crystallized from the heptane filtrate. The solid was collected, washed with heptane, and air-dried to afford stearyl 4-dimethylaminobutyramide (40.23 g; 84% yield).

$^1$H NMR (300 MHz, CDCl$_3$) δ 6.43 (br s, 1H); 3.22 (q, 2H); 2.30 (t, 2H); 2.24 (t, 2H); 2.21 (s, 6H); 1.78 (m, 2H); 1.48 (m, 2H); 1.25 (s, 33H); 0.88 (t, 3H).

HPLC (150×4.6 mm Zorbax SB-C8 column, 80:20 (v:v) methanol:water (containing 0.1% trifluoroacetic acid) for 10 min, gradient to 100% methanol over 1 min, held at 100% methanol for 9 min, ELSD detection): $t_R$ 10.4 min.

Example 27

Preparation of 3-((4-Stearylamino-4-oxobutyl)dimethylammonio)-2-hydroxypropanesulfonate Stearyl 4-dimethylaminobutyramide (4.00 g; 10.45 mmol), sodium 3-chloro-2-hydroxypropanesulfonate (95%, 2.31 g; 11.2 mmol; 1.07 equiv), and sodium carbonate (111 mg; 1.05 mmol; 0.1 equiv) were combined with 9 mL of isopropanol and 1.5 mL of water in a vial and heated to 81° C. for 18 hours to afford 99.8% conversion to product according to HPLC analysis.

The mixture was diluted with water resulting in a homogeneous solution. Isopropanol was added and the volatiles were evaporated. The residue was treated with MIBK and concentrated twice. The residue was diluted with 20 mL of MIBK and allowed to sit overnight resulting in a solid, which was filtered, washed with acetone, and air-dried to afford 4.40 g of 3-((4-stearylamino-4-oxobutyl)dimethylammonio)-2-hydroxypropanesulfonate as a white solid. $^1$H NMR was consistent with the product structure.

HPLC (150×4.6 mm Zorbax SB-C8 column, 80:20 (v:v) methanol:water (containing 0.1% trifluoroacetic acid) for 10 min, gradient to 100% methanol over 1 min, held at 100% methanol for 9 min, 220 nm detection): $t_R$ 13.4 min.

Comparative Example 1

Preparation of Lauryl N,N-Dimethylglycinate

Methyl 2-dimethylaminoacetate (189 g; 1.61 mol; 1.5 equiv), lauryl alcohol (200 g; 1.07 mol), and Novozym 435 (20 g) were combined in a 1 L 3-neck flask equipped with a Dean-Stark trap. 80 mL of heptane was added. The mixture was heated in a 65° C. bath, and the pressure was reduced until a good overhead flow of the heptane/methanol azeotrope was obtained (ca. 110 mm Hg). After 5 h, 99.1% conversion to product was observed by NMR analysis.

The reaction mixture was filtered to remove enzyme, the enzyme was washed with heptane, and the combined filtrate was concentrated to afford 289 g of lauryl N,N-dimethylaminoglycinate (99% yield).

$^1$H NMR (500 MHz, CDCl$_3$) δ 4.13 (t, 2H); 3.16 (s, 2H); 2.35 (s, 6H); 1.64 (m, 2H); 1.26 (s, 18H); 0.88 (t, 3H).

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, ELSD detection): $t_R$ 5.2 min.

Comparative Example 2

Preparation of 3-((Lauryloxycarbonylmethyl)dimethylammonio)-propanesulfonate 1,3-Propanesultone (18.2 g; 149 mmol; 1.01 equiv) was weighed into a 1 L round bottom flask. Lauryl 2-dimethylaminoacetate (40.0 g; 147 mmol) was dissolved in 200 mL of MIBK and added to the flask. The reaction mixture was heated in a 100° C. oil bath for 5 hours to afford 98.5% conversion to product according to HPLC analysis.

The reaction mixture was cooled to room temperature. The precipitate was collected by filtration, washed with MIBK, and air dried to afford 55 g (95% yield) of 3-((lauryloxycarbonylmethyl)dimethylammonio)-propane- sulfonate as a white solid with >99.9 wt % purity according to HPLC analysis. $^1$H NMR was consistent with the product structure.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, ELSD detection): $t_R$ 5.8 min.

Comparative Example 3

Preparation of Lauryl N,N-Dimethylaminoacetamide

Methyl 2-dimethylaminoacetate (28.4 g; 243 mmol; 1.5 equiv), lauryl amine (30 g; 162 mmol), and Novozym 435

(3.0 g) were combined in a 250 mL 3-neck flask equipped with a Dean-Stark trap, and 10 mL of heptane was added. The mixture was heated in a 65° C. oil bath and the pressure was reduced until a good overhead flow of the heptane/methanol azeotrope was obtained (ca. 150 mm Hg). After 2.5 h, 99.6% conversion to product was observed by HPLC analysis.

The reaction mixture was filtered to remove enzyme, the enzyme was washed with heptane, and the combined filtrate was concentrated to afford 42 g of lauryl N,N-dimethylaminoacetamide (96% yield).

$^1$H NMR (500 MHz, DMSO-$d_6$) δ 7.65 (br s, 1H); 3.05 (q, 2H); 2.81 (s, 2H); 2.18 (s, 6H); 1.39 (m, 2H); 1.23 (s, 18H); 0.85 (t, 3H).

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, ELSD detection): $t_R$ 4.6 min.

Comparative Example 4

Preparation of 3-((2-Laurylamino-2-oxoethyl)dimethylammonio)-propanesulfonate

Lauryl N,N-dimethylaminoacetamide (174 g, 643 mmol) and methyl isobutyl ketone (870 mL) were added to a 3 L round-bottom flask fitted with a thermocouple, overhead stirrer, and coiled reflux condenser with nitrogen head. 1,3-Propanesultone (79.0 g, 650 mmol; 1.01 equiv) was then added to the mixture. The reaction was heated to an internal temperature of 100° C. After 5 hours, heating was discontinued. Upon cooling to ambient temperature, the resulting slurry was filtered using a 2 L fritted funnel. The filter cake was washed with acetone until the filtrate was clear. The solid was placed in a 50° C. vacuum oven with nitrogen sweep to constant weight to afford 3-((2-Laurylamino-2-oxoethyl)dimethylammonio)propanesulfonate (227 g, 89.7% yield) as a white solid. $^1$H NMR was consistent with the product structure.

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, ELSD detection): $t_R$ 5.2 min.

Example 28

Comparison of Water Solubility of 3-((Lauryloxycarbonylpropyl)dimethylammonio)propanesulfonate Versus 3-(Lauryloxycarbonylmethyl)dimethylammonio)propanesulfonate $R^1$=Propyl To a vial was added 5.00 g of 3-((lauryloxycarbonylpropyl)-dimethylammonio)propanesulfonate and 10.00 g of water. The mixture was heated to 100° C. for an hour to afford a clear solution. The mixture was then allowed to cool to ambient temperature, at which point it was still homogeneous with no precipitate or gel. This indicates that the solubility of 3-((lauryloxycarbonylpropyl)dimethylammonio)propanesulfonate in water is greater than or equal to 33 wt %.

$R^1$=Methyl

To a vial was added 5.00 g of 3-((lauryloxycarbonylmethyl)-dimethylammonio)propanesulfonate and 45.00 g of water. The mixture was heated to 100° C. for an hour to afford a clear solution. The mixture was then allowed to cool to ambient temperature resulting in a white solid. The solid was recovered by filtration and dried in a vacuum oven at 55° C. in vacuo with a nitrogen sweep overnight to afford 4.58 g of 3-((lauryloxycarbonylmethyl)-dimethylammonio)propanesulfonate. This indicates that 0.42 g of 3-((lauryloxycarbonylmethyl)dimethylammonio)propanesulfonate remained soluble in 45 g of water at ambient temperature for a solubility limit of 0.92 wt %.

Example 29

Comparison of Water Solubility of 3-((4-Laurylamino-4-oxobutyl)dimethylammonio)propanesulfonate Versus 3-((2-Laurylamino-2-oxoethyl)dimethylammonio)propanesulfonate $R^1$=Propyl To a vial was added 10.00 g of 3-((4-laurylamino-4-oxobutyl)-dimethylammonio)propanesulfonate and 20.00 g of water. The mixture was heated to 100° C. for an hour to afford a clear solution. The mixture was then allowed to cool to ambient temperature, at which point it was still homogeneous with no precipitate or gel. This indicates that the solubility of 3-((4-laurylamino-4-oxobutyl)dimethylammonio)propanesulfonate in water is greater than or equal to 33 wt %.

$R^1$=Methyl

The solubility of 3-((2-laurylamino-2-oxoethyl)dimethylammonio)-propanesulfonate was determined by mixing 5.00 g of material with 45.00 g of water and heating to 85° C. for 1 h to afford a clear 10 wt % solution. The material was allowed to cool to ambient temperature to afford a precipitate. The precipitate was filtered, and the resulting solid was dried in vacuo at 50° C. with a nitrogen sweep for 3 days to afford 4.54 g of recovered 3-((2-laurylamino-2-oxoethyl)dimethylammonio)propanesulfonate. This indicates that 0.46 g of 3-((2-laurylamino-2-oxoethyl)dimethylammonio)-propanesulfonate remained soluble in 45 g of water at ambient temperature for a solubility limit of 1.02 wt %.

Surfactant Properties

The surfactant properties of the compounds of the formula 1 can be determined by a number of tests including an ASTM foam height test and a test for critical micelle concentration.

The Standard Test Method for Foaming Properties of Surface-Active Agents (ASTM 1173-07) for 0.1 wt % and 1.0 wt % was used to determine the foaming properties of the amphoteric compounds of the formula 1 described herein. This method generates foam under low-agitation conditions and is generally used for moderate- and high-foam surfactants. This test gathers data on initial foam height and foam decay. Foam decay provides information on foam stability.

The apparatus for carrying out this test includes a jacketed column and a pipet. The jacketed column serves as a receiver, while the pipet delivers the surface-active solution.

Solutions of each surface-active agent to be measured were prepared in borosilicate glass jars a day ahead of time, using ambient temperature ingredients, and were slowly rolled overnight to homogenize. The solutions were then removed from the rollers and equilibrated in a constant temperature bath (49° C.+/−1° C.) for at least 1 hour before measurement. The solution of the amphoteric compound to be tested was added to the receiver (50 mL) and to the pipet (200 mL). The pipet was positioned above the receiver and opened. As the solution fell and made contact with the solution in the receiver, foam was generated. When the pipet was empty, the time was noted and an initial foam height was recorded. The foam height was recorded each minute for five minutes. Exact size specifications for the glassware can be found in ASTM 1173-07. The foam height results for each amphoteric compound 1 and representative standards are listed below in Tables 1 (0.1% concentration) and 2 (1% concentration).

TABLE 1

Foam height (mm) at time t (min) at 0.1 wt % concentration

| | Foam height (mm) at time t (min) 1 g/L (0.1 weight %) | | | | | |
|---|---|---|---|---|---|---|
| | t = 0 | 1 | 2 | 3 | 4 | 5 |
| Standards | | | | | | |
| cocamidopropyl betaine | 160 | 159 | 158 | 158 | 158 | 158 |
| ExampleNo. | | | | | | |
| 3 | 171 | 170 | 170 | 169 | 169 | 169 |
| 4 | 142 | 139 | 135 | 132 | 129 | 127 |
| 5 | 157 | 154 | 151 | 149 | 147 | 146 |
| 9 | 185 | 175 | 173 | 170 | 170 | 170 |
| 11 | 174 | 172 | 171 | 171 | 170 | 170 |
| 12 | 160 | 157 | 155 | 153 | 151 | 150 |
| 14 | 143 | 133 | 123 | 108 | 95 | 75 |
| 16 | 158 | 157 | 156 | 155 | 155 | 154 |
| 17 | 148 | 145 | 143 | 142 | 140 | 140 |
| 20 | 180 | 175 | 170 | 170 | 170 | 170 |
| 21 | 157 | 156 | 153 | 151 | 149 | 147 |
| 24 | 157 | 156 | 156 | 156 | 156 | 155 |

TABLE 2

Foam height (mm) at time t (min) at 1.0 wt % concentration

| | Foam height (mm) at time t (min) 10 g/L (1.0 weight %) | | | | | |
|---|---|---|---|---|---|---|
| | t = 0 | 1 | 2 | 3 | 4 | 5 |
| Standards | | | | | | |
| cocamidopropyl betaine | 174 | 172 | 171 | 171 | 170 | 170 |
| ExampleNo. | | | | | | |
| 3 | 165 | 162 | 160 | 158 | 158 | 156 |
| 4 | 173 | 170 | 167 | 162 | 158 | 154 |
| 5 | 170 | 166 | 161 | 158 | 154 | 152 |
| 8 | 185 | 175 | 170 | 170 | 170 | 165 |
| 9 | 195 | 190 | 180 | 180 | 180 | 180 |
| 11 | 182 | 180 | 179 | 178 | 178 | 177 |
| 12 | 182 | 180 | 178 | 177 | 176 | 175 |
| 14 | 157 | 145 | 137 | 129 | 122 | 116 |
| 16 | 177 | 175 | 173 | 172 | 170 | 170 |
| 17 | 174 | 170 | 168 | 167 | 166 | 165 |
| 20 | 175 | 170 | 170 | 170 | 165 | 160 |
| 21 | 173 | 171 | 170 | 170 | 170 | 169 |
| 24 | 171 | 169 | 167 | 165 | 163 | 161 |

As the data in Tables 1 and 2 indicate, solutions of the amphoteric compounds 1 generated large amounts of foam. Examples in which the foam height did not significantly decrease over time indicate good foam stability.

Surfactants are amphiphilic molecules that tend to adsorb at surfaces or interfaces spontaneously. Surface tension is a measure of the work required to increase surface area of a liquid-gas interface by unit amount, and is a consequence of the inhomogeneity of molecular cohesive interactions at the interface compared with molecules in the bulk. Under ideal conditions for surfactants in deionized water, the measured surface tension gradually decreases from the pure water surface tension value with increasing surfactant concentration to a minimum that occurs when the surface is fully saturated. The initial gradual decrease in surface tension is due to adsorption of surfactant molecules of lower cohesive energy at the interface in place of water molecules that have higher cohesive energy. For surfactants that self-assemble in solution, once the interface is saturated additional surfactant molecules added to solution will tend to aggregate into structures called micelles, so surface tension remains essentially constant upon increase in surfactant concentration.

The critical micelle concentration (CMC) is an important characteristic of a surfactant, and the CMC values were determined for the amphoteric compounds of formula 1. The CMC is defined as the concentration at which micelle formation first begins, and for surface tension determination of CMC, is typically assigned as the concentration of the intersection of two straight lines through the data, where the first line is the linear portion of the initial decline in surface tension with increasing surfactant concentration, and the second is the line of constant surface tension.

A lower CMC value is desirable and indicates less surfactant is needed to saturate interfaces and form micelles. Typical CMC values are less than 1 weight percent (10,000 ppm).

The critical micelle concentration was determined from plots of surface tension as a function of the logarithm of active surfactant concentration. Surface tension was measured via the Wilhelmy plate technique. In this method, the downward force of a rigorously clean plate probe that just contacts the liquid surface of the test sample is measured, and the surface tension is calculated from knowledge of the contact angle the liquid makes with the probe surface and the length of the probe plate.

A K100C Tensiometer (Kruss GmbH) was used to measure surface tension of solutions in a glass sample vessel. All measurements were made under ambient temperature conditions.

The tensiometer was equipped with a computer-controlled microdispensing and aspirating system to automate surfactant concentration adjustments of the test solution while maintaining constant solution volume between successive measurements. A roughened platinum plate probe was used. Cleanliness of probe, sample vessel, and microdispensing system was verified after cleaning between samples by measuring the surface tension of pure deionized water run through the system as a control.

100 mL of the 1 mg/L surfactant solution was added to the clean sample vessel and placed in the instrument. The plate probe was rinsed with deionized water and flame treated to combust off residual organic impurities, then mounted in position in the tensiometer. The experiment was initiated and run through the LabDesk version 3.2.2 (Kruss GmbH) software.

The surface tension measurements were run sequentially (and automatically) from most dilute to most concentrated by incrementally injecting known volume aliquots of the 10,000 mg/L surfactant solution into the sample, homogenizing the sample after injection by stirring for 30 seconds via a magnetic stir bar in the solution, and then aspirating out equal volume that was added to the sample vessel to keep the total sample volume constant for each measurement.

The sample vessel was then automatically moved into measurement position, and the surface tension measurement was made and recorded. This sequence was repeated until all concentrations had been measured.

The active surfactant concentration range spanned from 1 mg/L to 5000 mg/L over 50 concentration increments, equally spaced on a logarithmic scale over the full range of concentrations measured.

The sample at each concentration was measured 10 times, and the average of the 10 measures was plotted against the logarithm of the surfactant concentration.

After completing the full range of concentrations, the software provided best-fit lines to estimate CMC, and these regression lines were manually adjusted as needed to give the broadest range of linear behavior for each line. Generally, these manual adjustments resulted in a range of potential CMC values that spanned 1-3 mg/L, and this range can be considered to be an estimate of uncertainty in the reported CMC.

TABLE 3

Critical micelle concentrations

| | CMC (mg/L) |
|---|---|
| Standards | |
| N-lauryl-N,N-dimethyl-3-ammonio-1-propanesulfonate | 962 |
| cocamidopropyl betaine | 12.7 |
| cocamidopropyl hydroxysultaine | 9.5 |
| Compound from Example No. | |
| 3 | 24.2 |
| 5 | 53.9 |
| 11 | 76.5 |
| 12 | 80.9 |
| 14 | 133.9 |
| 16 | 5.8 |
| 17 | 6.4 |
| 21 | 104.5 |
| 24 | 7.9 |

The data in Table 3 indicate that very low concentrations of the amphoteric compounds 1 are needed to reach the critical micelle concentration. These values fall in the range of useful surface-active agents, and compare well with standard surfactants.

The invention has been described in detail with particular reference to preferred embodiments thereof, but it will be understood that variations and modifications can be effected within the spirit and scope of the invention.

We claim:

1. A mixture comprising at least two compounds having the formula 1:

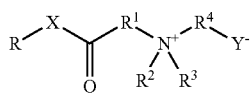

wherein the at least two compounds have at least one different R substituent and R is lauryl, myristyl, or a $C_6$ to $C_{20}$ alkyl radical derived from a vegetable oil, a nut oil, or a seed oil;

$R^1$ is 1,4-butylene;

$R^2$ and $R^3$ are both methyl;

$R^4$ is 2-hydroxy-1,3-propylene;

X is NH; and $Y^-$ is $SO_3^-$.

2. The mixture according to claim 1, wherein the seed oil comprises coconut oil, hydrogenated coconut oil, palm kernel oil, or hydrogenated palm kernel oil.

3. The mixture according to claim 1, which has a solubility of at least 5 wt % in water at 20 to 50° C.

4. The mixture according to claim 1, which has a solubility of at least 30 wt % in water at 20 to 50° C.

5. A mixture comprising at least two compounds having the formula 1:

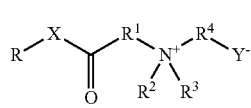

wherein the at least two compounds have at least one different R substituent and R is a $C_3$-$C_{24}$ hydrocarbyl group;

$R^1$ is a $C_2$-$C_8$ hydrocarbyl group;

$R^2$ and $R^3$ are each independently a $C_1$-$C_6$ alkyl or alkenyl group;

at least two of $R^1$, $R^2$, and $R^3$ are connected with the $N^+$ to form a heterocyclic ring;

$R^4$ is a $C_1$-$C_8$ hydrocarbyl group;

X is O or NH; and $Y^-$ is $SO_3^-$, $SO_4^-$, $PO_3^{-2}$, or $PO_4^{-2}$.

6. The mixture according to claim 5, wherein the heterocyclic ring is selected from the group consisting of pyrrolidinium, piperidinium, pyridinium, quinolinium, tetrahydroquinolinium, indolinium, octahydroindolinium, acridinium, octahydroacridinium, and tetradecahydroacridinium.

7. The mixture according to claim 5, wherein

R is lauryl, myristyl, cetyl, stearyl, or a $C_6$ to $C_{20}$ alkyl radical derived from a vegetable oil, a nut oil, or a seed oil;

$R^1$ and $R^2$ combine with the $N^+$ to form a 3-piperidininum, a 4-piperidinium, a 3-piperidiniummethyl, a 4-piperidiniummethyl, a 3-pyridinum, a 4-pyridinium, a 3-pyridiniummethyl, or a 4-pyridiniummethyl group;

$R^3$ is methyl;

$R^4$ is methylene, ethylene, propylene, butylene, or hydroxypropylene;

X is O or NH; and $Y^-$ is $SO_3^-$.

8. The mixture according to claim 7, wherein the seed oil comprises coconut oil, hydrogenated coconut oil, palm kernel oil, or hydrogenated palm kernel oil.

9. The mixture according to claim 8, wherein X is NH.

* * * * *